United States Patent [19]

Chowhan

[11] Patent Number: 5,342,620
[45] Date of Patent: Aug. 30, 1994

[54] USE OF BORATE-POLYOL COMPLEXES IN OPHTHALMIC COMPOSITIONS

[75] Inventor: Masood Chowhan, Arlington, Tex.

[73] Assignee: Alcon Laboratories, Inc., Fort Worth, Tex.

[21] Appl. No.: 118,833

[22] Filed: Sep. 7, 1993

Related U.S. Application Data

[63] Continuation of Ser. No. 879,435, May 6, 1992, abandoned.

[51] Int. Cl.$^5$ .............................................. A61K 9/08
[52] U.S. Cl. ................................. 424/422; 424/400; 424/427; 424/658; 424/659; 514/839; 514/840; 514/912; 514/915
[58] Field of Search ............... 424/400, 427, 658, 659; 514/839, 840, 912, 915

[56] References Cited

U.S. PATENT DOCUMENTS

| | | | |
|---|---|---|---|
| 4,029,817 | 6/1977 | Blanco et al. | 424/78.04 |
| 4,581,379 | 4/1986 | Nelson et al. | 514/840 |
| 4,710,313 | 12/1987 | Miyajima et al. | 514/839 |
| 4,748,189 | 5/1988 | Su et al. | 514/915 |
| 4,820,352 | 4/1989 | Riedhammer et al. | 514/839 |
| 4,960,799 | 10/1990 | Nagy | 514/912 |
| 5,032,392 | 7/1991 | Varma | 424/78.04 |
| 5,141,665 | 8/1992 | Sherman | 514/840 |

FOREIGN PATENT DOCUMENTS

0109561A1 5/1984 European Pat. Off. .
0436726A1 7/1991 European Pat. Off. .
2230358 12/1974 France .

OTHER PUBLICATIONS

Rakow, P. L. *Contact Lens Forum* (Jun., 1988), 41–46.
Okada, T. *J. Chromatography*, 403:27-33 (1987).
Sciarra, J. et al., *J. Am. Pharm. Assoc.*, 49(2):115-117 (1960).
Morawetz, H., "Macromolecules In Solution," John Wiley & Sons, Inc., New York: 1974, pp. 402–404.
Gilman, H. et al. (eds.), "Organic Chemistry" vol. I, John Wiley & Sons, Inc. New York: 1950, pp. 432–433.
Gilman, H. et al. (eds.), "Organic Chemistry" vol. II, John Wiley & Sons, Inc., New York: 1950, pp. 1540–1542, 1588, 1589, 1606–1610.

*Primary Examiner*—Thurman K. Page
*Assistant Examiner*—Amy Hulina
*Attorney, Agent, or Firm*—Julie J. L. Cheng

[57] ABSTRACT

Aqueous ophthalmic compositions containing water-soluble borate-polyol complexes are useful in aqueous ophthalmic compositions containing polyvinyl alcohol. These compositions provide the benefits of a borate buffering system, such as enhanced antimicrobial activity, without the problems associated with the use of borate and pol, such as formation of borate-polyvinyl alcohol complexes which are water-insoluble.

15 Claims, No Drawings

USE OF BORATE-POLYOL COMPLEXES IN OPHTHALMIC COMPOSITIONS

This application is a continuation of application Ser. No. 07/879,435, filed May 6, 1992, now abandoned.

BACKGROUND OF THE INVENTION

This invention relates to the use of borate-polyol complexes in ophthalmic compositions. In particular, these complexes are useful in aqueous ophthalmic compositions containing polyvinyl alcohol to prevent the formation of borate-polyvinyl alcohol complexes, which are water-insoluble.

Ophthalmic compositions are generally formulated to have a pH between about 4.5 and 8.0 (physiological pH). To achieve a pH in this range, a buffer is often included. Borate buffer is the buffer of choice for use in ophthalmic compositions, since it has some inherent antimicrobial activity and often enhances the activity of antimicrobials; however, when polyvinyl alcohol (PVA) is also an ingredient in the composition, borate and PVA form a water-insoluble complex which precipitates out of solution and acts as an irritant in the eye. The incompatibility of borate and PVA in contact lens solutions has been discussed in an article by P. L. Rakow in *Contact Lens Forum*, (June 1988), pages 41–46.

Since borate is incompatible with PVA, ophthalmic compositions containing PVA are generally buffered with acetate, phosphate or other buffers. There are disadvantages to using these alternative buffers: for example, acetate is a weak buffer ($pK_a$ of about 4.5), so a relatively large amount is needed, whereas phosphate is a good buffer, but it reduces the antimicrobial activity of preservatives. A need therefore exists for ophthalmic compositions which have a physiological pH, but whose antimicrobial efficacy is not compromised.

SUMMARY OF THE INVENTION

This invention provides such compositions. Ophthalmic compositions containing the borate-polyol complexes of the present invention have physiological pH and additionally have very good antimicrobial activity. Moreover, compositions containing these complexes have reduced toxicity over compositions formulated with other types of buffering agents. The borate-polyol complexes are formed by mixing borate and/or boric acid with polyols, such as mannitol or glycerin, in an aqueous solution. The resultant solution may then be used as a buffer in formulating aqueous ophthalmic compositions, even where such compositions also contain PVA.

These compositions are particularly useful in contact lens care products which are targeted for wearers of rigid gas-permeable contact lenses (RGPs). Wearers of RGPs often complain of discomfort. PVA is a viscosity enhancer and is used extensively in all types of RGP products in order to improve the comfort and wearing time of RGPs. PVA is also extensively used as a viscosity enhancer for pharmaceutical ophthalmic compositions such a eye drops, gels or ocular inserts. Such compositions would also be improved by the use of the borate-polyol complexes of the present invention.

The borate-polyol complexes of the present invention are also useful in contact lens disinfecting solutions. When these borate-polyol complexes are included in contact lens disinfecting solutions containing quaternary ammonium compounds (e.g., benzalkonium chloride), biguanides (e.g., chlorhexidine) or polymeric antimicrobials, such as polymeric quaternary ammonium compounds (e.g., Polyquad®, Alcon Laboratories, Inc., Fort Worth, Tex.) or polymeric biguanides (e.g., Dymed®, Bausch & Lomb, Rochester, N.Y.), there is enhanced antimicrobial activity. It is believed that this enhancement is due to a reduction in the amount of binding or complexing of the antimicrobial to the buffers.

DETAILED DESCRIPTION OF THE INVENTION

The ophthalmic compositions of the present invention comprise PVA and water-soluble borate-polyol complexes, such as those described by T. Okada in *J. Chromatography*, 403:27–33 (1987) and by J. Sciarra et al. in *J. Am. Pharm. Assoc.*, 49(2):115–117 (1960). The contents of these two articles are incorporated herein by reference to the extent that they describe borate-polyol complexes.

As used herein, the term "borate" shall refer to boric acid, pharmaceutically acceptable borates, or combinations thereof. Most suitable are: boric acid, sodium borate, calcium borate, magnesium borate, manganese borate, and other such borate salts.

As used herein, and unless otherwise indicated, the term "polyol" shall refer to any compound having at least two adjacent —OH groups which are not in trans configuration relative to each other. The polyols can be linear or circular, substituted or unsubstituted, or mixtures thereof, so long as the resultant complex is water-soluble and pharmaceutically acceptable. Such compounds include sugars, sugar alcohols, sugar acids and uronic acids. Preferred polyols are sugars, sugar alcohols and sugar acids, including, but not limited to: mannitol, glycerin, propylene glycol and sorbitol. Especially preferred polyols are mannitol and glycerin; most preferred is mannitol.

The water-soluble borate-polyol complexes of the present invention may be formed by mixing borate with the polyol(s) of choice in an aqueous solution. In general, the molar ratio of borate to polyol is between about 1:1 and about 1:10. Some borate-polyol complexes, such as potassium borotartrate, are commercially available.

The borate-polyol complexes are utilized in the compositions of the present invention in an amount between about 0.5 to about 6.0 percent by weight (wt %), preferably between about 1.0 to about 2.5 wt %.

PVA is available in a number of grades, each differing in degree of polymerization, percent of hydrolysis, and residual acetate content. Such differences affect the physical and chemical behavior of the different grades. PVA can be divided into two broad categories, i.e., completely hydrolyzed and partially hydrolyzed. Those containing 4% residual acetate content or less are referred to as completely hydrolyzed. Partially hydrolyzed grades usually contain 20% or more residual acetate. The molecular weight of PVA's vary from 20,000 to 200,000. In general, PVA used in ophthalmic products has an average molecular weight in the range of 30,000 to 100,000 with 11% to 15% residual acetate. Compositions of the present invention generally contain PVA at a concentration less than about 10.0 wt %, preferably between about 0.1 and about 1.4 wt % and most preferably at a concentration of about 0.75 wt %.

EXAMPLE 1

The water-soluble borate-polyol complexes of the present invention may be prepared as illustrated below.

TABLE 1

| INGREDIENT | A | B | C | D | E | F | G | H |
|---|---|---|---|---|---|---|---|---|
| | | | | FORMULATION | | | | |
| Boric Acid | 0.35 | 0.35 | 0.35 | 0.35 | 0.35 | 0.35 | 0.35 | 0.35 |
| Sodium Borate | 0.11 | 0.11 | 0.11 | 0.11 | 0.11 | 0.11 | 0.11 | 0.11 |
| Mannitol | 0.5 | 1.0 | 1.5 | 2.0 | — | — | — | — |
| Glycerin | — | — | — | — | 0.5 | 1.0 | 1.5 | 2.0 |
| Na$_2$EDTA | 0.1 | 0.1 | 0.1 | 0.1 | 0.1 | 0.1 | 0.1 | 0.1 |
| Purified Water | q.s. | q.s. | q.s. | q.s. | q.s. | q.s. | q.s. | q.s. |
| HCl/NaOH | pH 7.4 | pH 7.4 | pH 7.4 | pH 7.4 | pH 7.4 | pH 7.4 | pH 7.4 | pH 7.4 |
| Polyquad ® | 0.0001 + 10% xs | 0.001 + 10% xs | 0.001 + 10% xs | 0.001 + 10% xs | 0.001 + 10% xs | 0.001 + 10% xs | 0.001 + 10% xs | 0.001 + 10% xs |

Preparation

Formulations A–H were prepared as follows. Tubular, labeled and calibrated 150 milliliter (ml) beakers were each filled with about 90 ml of purified water. Boric acid, sodium borate and mannitol or glycerin were then added and dissolved by stirring the solution for about 25 minutes. At this time, disodium EDTA (ethylene diamine tetraacetic acid) was added with stirring. Purified water was added to bring the solutions almost to 100% (100 ml), pH was adjusted to approximately 7.4 and the osmolality was measured. Polyquad ® was then added and the volume brought to 100% by the addition of purified water. pH was again measured and adjusted, if necessary, and the osmolality was measured again.

It is not always necessary to have an isotonic solution; however, if there is a need to have an isotonic solution, the osmolality can be adjusted by incorporating polyol with OH groups in trans position, sodium chloride, potassium chloride, calcium chloride or other osmolality building agents which are generally acceptable in ophthalmic formulations.

EXAMPLE 2

Aqueous ophthalmic compositions of the present invention may be prepared using the formulations illustrated below.

Preparation

Formulations 1-9 were prepared as follows. A first solution (Solution A) was prepared by adding 500 ml of warm purified water to a calibrated two liter aspirator bottle equipped with a magnetic stirrer. PVA and hydroxyethyl cellulose were then added to Solution A and the contents dispersed by stirring. After dispersal of the polymers, a filter assembly was attached to the aspirator bottle (142 mm Millipore filter holder with 0.2 μ filter), and this whole apparatus autoclaved at 121° C. for 30 minutes. Solution A with the filter assembly attached was then allowed to cool to room temperature with stirring. A second solution (Solution B), was prepared in a 500 ml beaker containing 300 ml of purified water by adding boric acid, sodium borate and mannitol and dissolving the contents by stirring for 25 minutes. Edetateidisodium, sodium chloride, preservatives and other osmolality-building agents, as necessary, were added to Solution B and the contents dissolved with stirring. Solution B was then sterile filtered into the aspirator bottle containing Solution A. The pH of the resultant solution was then adjusted and the volume brought to 100% by sterile filtering purified water.

EXAMPLE 3

The following ophthalmic compositions of the present invention may also be prepared using the procedure detailed in Example 2.

TABLE 2

| INGREDIENT | 1 | 2 | 3 | 4 | 5 | 6 | 7 | 8 | 9 |
|---|---|---|---|---|---|---|---|---|---|
| | | | | | FORMULATION | | | | |
| PVA | 0.75 | 1.4 | 0.75 | 0.75 | 0.75 | 0.75 | 0.75 | 0.75 | 0.75 |
| HEC | — | — | 0.75 | 0.28 | 0.28 | 0.28 | 0.28 | 0.75 | 0.75 |
| Mannitol | 2.0 | 2.0 | 2.0 | 2.0 | 2.0 | 2.0 | 0.5 | 2.0 | 2.0 |
| Boric Acid | 0.35 | 0.35 | 0.35 | 0.35 | 0.35 | 0.35 | 0.35 | 0.35 | 0.35 |
| Sodium Borate | 0.11 | 0.11 | 0.11 | 0.11 | 0.11 | 0.11 | 0.11 | 0.11 | 0.11 |
| Edetate Disodium | 0.1 | 0.1 | 0.1 | 0.1 | 0.1 | 0.1 | 0.1 | 0.1 | 0.1 |
| Sodium Chloride | 0.09 | 0.09 | 0.09 | 0.09 | 0.45 | 0.09 | 0.09 | 0.09 | 0.09 |
| Polyquad ® | 0.001 | 0.001 | 0.001 | 0.001 | 0.001 | 0.001 | 0.001 | — | — |
| Sucrose | — | — | — | — | — | 2.5 | — | 2.5 | 2.5 |
| Polyhexamethylene Biguanide | — | — | — | — | — | — | — | 0.0005 | — |
| BAC | — | — | — | — | — | — | — | — | 0.004 |

TABLE 3

| INGREDIENT | 1 | 2 | 3 | 4 | 5 | 6 | 7 | 8 | 9 | 10 |
|---|---|---|---|---|---|---|---|---|---|---|
| | | | | | FORMULATIONS | | | | | |
| PVA | 1.4 | 1.4 | 1.4 | 1.4 | 1.4 | 1.4 | 1.4 | 1.4 | 1.4 | 1.4 |
| Naphazolene HCl | 0.1 | 0.1 | — | — | — | — | — | — | — | — |

TABLE 3-continued

| INGREDIENT | FORMULATIONS | | | | | | | | | |
|---|---|---|---|---|---|---|---|---|---|---|
| | 1 | 2 | 3 | 4 | 5 | 6 | 7 | 8 | 9 | 10 |
| Sodium Sulfacetamide | — | — | — | 10.0 | — | — | — | — | — | — |
| Fluorometholone | — | — | — | — | 0.1 | — | — | — | — | — |
| Gentamicin Sulfate | — | — | — | — | — | 0.4 | — | — | — | — |
| Levobunolol HCl | — | — | 0.5 | — | — | — | — | — | — | — |
| Mydrysone | — | — | — | — | — | — | 1.0 | — | — | — |
| Pilocarpine Nitrate | — | — | — | — | — | — | — | 1.0 | 1.0 | 1.0 |
| Sodium Metabisulfite | — | — | 0.4 | — | — | — | — | — | — | — |
| Mannitol | 2.0 | 2.0 | 2.0 | 2.0 | 2.0 | 2.0 | 2.0 | 2.0 | 4.0 | 0.5 |
| Boric Acid | 0.35 | 0.35 | 0.35 | 0.35 | 0.35 | 0.35 | 0.35 | 0.35 | 0.35 | 0.5 |
| Sodium Borate | 0.11 | 0.11 | 0.11 | 0.11 | 0.11 | 0.11 | 0.11 | 0.11 | — | — |
| Sodium Chloride | 0.45 | 0.45 | 0.45 | — | 0.45 | 0.45 | 0.45 | 0.45 | — | — |
| Edetate Disodium | 0.1 | 0.1 | 0.1 | 0.1 | 0.1 | 0.1 | 0.1 | 0.1 | 0.1 | 0.1 |
| BAC | 0.004 | — | — | — | — | — | — | — | — | — |
| Polyquad ® | — | 0.001 | 0.001 | 0.001 | 0.001 | 0.001 | 0.001 | 0.001 | 0.001 | 0.001 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A method of preparing an aqueous ophthalmic composition, comprising the steps of preparing a water-soluble borate-polyol complex by mixing borate and a polyol together in a aqueous solvent and adding polyvinyl alcohol thereto, wherein the water-soluble borate-polyol complex is present at a concentration between about 0.5 to about 6.0 wt %.

2. An aqueous ophthalmic composition prepared in accordance with the method of claim 1, comprising polyvinyl alcohol and a water-soluble borate-polyol complex, wherein the water-soluble borate-polyol complex is present at a concentration between about 0.5 to about 6.0 wt %.

3. The aqueous composition of claim 2, wherein the water-soluble borate-polyol complex comprises borate and polyol in a molar ratio between about 1:1 and about 1:10.

4. The aqueous composition of claim 2, wherein the water-soluble borate-polyol complex is present at a concentration between about 1.0 and about 2.5 wt %.

5. The aqueous composition of claim 2, wherein the water-soluble borate-polyol complex comprises a polyol selected from the group consisting of sugars, sugar alcohols and sugar acids.

6. The aqueous composition of claim 3, wherein the polyol is selected from the group consisting of mannitol, glycerin, propylene glycol and sorbitol.

7. The aqueous composition of claim 6, wherein the polyol is selected from the group consisting of mannitol and glycerin.

8. The aqueous composition of claim 7, wherein the polyol is mannitol.

9. The method of claim 1, wherein the water-soluble borate-polyol complex comprises borate and polyol in a molar ratio between about 1:1 and about 1:10.

10. The method of claim 1, wherein the concentration of the water-soluble borate-polyol complex in the final composition is between about 0.5 and about 0.3 wt %.

11. The method of claim 10, wherein the concentration of the water-soluble borate-polyol complex in the final composition is between about 1.0 and about 2.0 wt %.

12. The method of claim 1, wherein the water-soluble borate-polyol complex comprises a polyol selected from the group consisting of sugars, sugar alcohols and sugar acids.

13. The method of claim 12, wherein the polyol is selected from the group consisting of mannitol, glycerin, propylene glycol and sorbitol.

14. The method of claim 13, wherein the polyol is selected from the group consisting of mannitol and glycerin.

15. The method of claim 14, wherein the polyol is mannitol.

* * * * *